United States Patent [19]

Kolesar, Jr.

[11] Patent Number: 4,906,440

[45] Date of Patent: Mar. 6, 1990

[54] SENSOR FOR DETECTING CHEMICALS

[75] Inventor: Edward S. Kolesar, Jr., Beavercreek, Ohio

[73] Assignee: The United States of America as represented by the Secretary of the Air Force, Washington, D.C.

[21] Appl. No.: 905,712

[22] Filed: Sep. 9, 1986

[51] Int. Cl.$^4$ ............................................. G01N 27/04
[52] U.S. Cl. ..................................... 422/98; 324/71 S; 338/34; 422/83; 422/88; 422/90; 436/104
[58] Field of Search ...................... 422/83, 88, 90, 98; 436/104; 338/34; 324/65 P

[56] References Cited

U.S. PATENT DOCUMENTS

| | | | |
|---|---|---|---|
| 3,144,850 | 8/1964 | Rosenberg | 116/67 |
| 3,428,892 | 2/1969 | Meinhard | 324/71.1 |
| 3,451,901 | 6/1969 | Seiger et al. | 204/1 |
| 3,989,463 | 11/1976 | Klein et al. | 23/254 E |
| 4,130,797 | 12/1978 | Hattori et al. | 422/98 |
| 4,305,724 | 12/1981 | Micko | 422/94 |
| 4,352,087 | 9/1982 | Wittmaier | 340/632 |
| 4,423,407 | 12/1983 | Zuckerman | 422/98 |
| 4,458,242 | 12/1984 | Kusanagi et al. | 422/98 |
| 4,517,161 | 5/1985 | Gravina et al. | 422/95 |
| 4,549,427 | 10/1985 | Kolesar, Jr. | 73/23 |

OTHER PUBLICATIONS

Epstein et al, "Kinetics of Some Metal Ion-catalyzed Hydrolyses of Isopropyl Methylphosphonofluoridate (GB) at 25°," Journal of the American Chemical Society, vol. 80, 1958, pp. 3596 to 3598.

T. Wagner-Jauregg et al, "Model Reactions of Phosphorus-containing Enzyme Inactivators. IV. The Catalytic Activity of Certain Metal Salts and Chelates in the Hydrolysis of Diisopropyl Fluorophosphate", Journal of American Chemical Society, vol. 77, 1955, pp. 922-929.

Kaufman, "Theory of a Monolithic Null Device and Some Novel Circuits", Proceedings of the IRE, vol. 48, Sep. 1960, pp. 1540-1545.

Gustafson et al, "A Kinetic Study of the Copper(II) Chelate Catalyzed Hydrolysis of Diisopropyl Phosphorofluoridate", Journal of Chemical Soc., vol. 85, 1963, pp. 598-601.

Murakami et al, "Kinetic Studies of the Catalytic Hydrolysis of 1,3-Dicarboxyphenyl 2-Phosphate and 1-Methoxycarbonyl-3-carboxyphenyl 2-Phosphate", Journal of the American Chemical Society, vol. 86, 1964, pp. 2119 to 2129.

Bilotti, "Operation of a MOS Transistor as a Variable Resistor", Proceedings of the IEEE, 1966, pp. 1093 to 1094.

Stein, "A New Look at Distributed RC Notch Filters", Proceedings of the IEEE, 1970, pp. 596-598.

Kolesar, "Bibliography" from Ph.D. Thesis, 1985, (available to public Oct. 1985).

Primary Examiner—Barry S. Richman
Assistant Examiner—Timothy M. McMahon
Attorney, Agent, or Firm—Stanton E. Collier; Donald J. Singer

[57] ABSTRACT

A sensor for a gas detector is provided that detects the presences of the gas when the gas reacts with a distributed Rc notch network to cause a shift in operating frequency and notch depth. A metallic/metallic oxide gas sensitive discontinuous film acts as the distributive resistive element in the RC notch network. The gas changes the conductivity of the film and this causes the network to react. In the preferred embodiment, a copper/cuprous oxide film detects organophosphorus compounds.

4 Claims, 3 Drawing Sheets

SENSOR FOR DETECTING CHEMICALS

STATEMENT OF GOVERNMENT INTEREST

The invention described herein may be manufactured and used by or for the Government for governmental purposes without the payment of any royalty thereon.

BACKGROUND OF THE INVENTION

The present invention relates to an electronic sensor for detecting chemical compounds, and, in particular, a sensor capable of detecting organophosphorus compounds and chemical warfare nerve agents.

In the course of daily activity, the living and working environment exposes man to a variety of toxic gases and vapors. Today, the circumstances in many industrial environments is particularly precarious, and this situation has motivated the establishment of specific exposure level guidelines and monitoring schemes for ensuring personal safety. One particular group of contaminants are the organophosphorus pesticides and structurally affiliated chemical warfare nerve agents. Adding to their impact, these organophosphorus compounds are synthesized and valued for their deleterious effect and persistence.

Several types of air pollution monitoring systems are available which lend themselves to varying degrees of portability. At one end of the technology spectrum, a sample of the atmosphere is taken and sent to a laboratory for analysis. This process is inconvenient, after the fact, expensive, and time consuming. At the other end of the technology spectrum, direct monitoring instruments are used to monitor a specific contaminant in a large work area. However, these systems tend to be bulky, complicated, expensive to purchase, operate and maintain, and fail to provide information on individual exposure.

It is well documented that a material's surface and electronic properties are strongly influenced by ambient conditions, but little progress has been made exploiting this phenomenon for the practical application of toxic gas detection. The primary problem involves identifying the fundamental electronic mechanisms and processes by which certain materials respond to gas ambients. A secondary problem encompasses the utilization of materials compatible with conventional integrated circuit fabrication technology, but yet retain sensitivity and selectivity to the toxic gas of interest.

One type of personal detector for nerve agents is a litmus type paper that is issued to GIs when in areas of potential danger. Nerve agents that are applied in a gaseous form, invisible to the eye, obviously would not be detected until it was too late to take effective action. The only warning would be the presence of bodies without injuries in an area. Typically, nerve agents are applied in an aerosol form from a bursting ordinance round or sprayed from an aircraft. The droplets would be found on the surface of clothing, vehicles, aircraft, etc. The litmus type paper is rubbed against the surface and if the particular agent is present, the paper changes color. Based upon the type of nerve agent found, the proper antidote can be administered. Given the proper warning, chemical warfare clothing can be used for protection until the agent is removed or neutralized. The above warnings, such as dud sounding ordinance, fog in low lying areas, stricken personnel, aircraft spraying may come too late for the GI in the field away from area electronic agent detectors.

Another type of detector has a housing for holding and protecting an electronic circuit and a pair of deflectable micromechanical cantilevers driven by oscillators. One of the pair of cantilevers is coated with a chemically selective substance to form an end-mass load. As the nerve agent of concern is absorbed by the selective substance, the end-mass changes and so does the resonant frequency of that coated cantilever. The uncoated cantilever acts as a standard frequency source to which the coated cantilever is compared. These frequencies are input to a mixer circuit that outputs the difference frequency. The difference frequency, after going through pulse shaping, is input to counter circuits that determine if a set limit is exceeded and, if so, how much is the limit exceeded by as a function of time. This detector is further described in U.S. Pat. No. 4,549,427 which is incorporated by reference. These deficiencies have motivated a search for alternative devices.

SUMMARY OF THE INVENTION

The present invention overcomes the problems encountered in the past, and described in detail herein, by providing an electronic sensor for detecting organophosphorus chemical warfare nerve agents.

The sensor for the personal detector of gaseous chemical compounds is a distributed RC notch network circuit. An insulating substrate has thereon a longitudinal strip of metal. Over the strip and the exposed substrate is deposited a layer of insulating material. One top of the insulating layer are deposited two metal rectangular islands. The islands are deposited adjacent to and on opposite sides of the strip and thus form the distributed capacitance of the RC notch network circuit. A discontinuous layer of chemically sensitive metal is deposited over the islands and the exposed insulating layer to form the distributed resistance element of the RC notch network circuit. When the specified chemical reacts with the discontinuous metal layer, it changes the electrical conductivity thereof. This change causes both the notch frequency and the notch depth to change. Because of the nonlinear behavior of the RC notch network circuit, a small change in the distributed resistance results in a much larger change in the notch frequency and depth, thus allowing the detection of very small quantities of chemical.

It is therefore an object of the present invention to provide a personal nerve agent detector.

It is a further object of the present invention to provide a nerve agent detector that is able to detect a wide variety of nerve agents, specifically organophosphorous agents.

It is a further object of the present invention to provide a nerve agent detector that is not affected by physical/environmental interferences.

It is a further object of the present invention to provide a detector that functions as a dosimeter.

It is a further object of the present invention to provide a sensor for the detector that has a non-linear response and thus able to detect very small quantities of the agents.

These and many other objects and advantages of the present invention will be readily apparent to one skilled in the pertinent art from the following detailed description of a preferred embodiment of the invention and the related drawings.

DETAILED DESCRIPTION OF THE PREFERRED EMBODIMENT

It has been noted in the past that a discontinuous metallic film's electrical conductivity is modified when it is removed from its high-vacuum deposition chamber, and subsequently exposed to the ambient atmosphere. The change in the electronic transport properties of these high surface area to volume ratio films may be a result of the following:

(1) The ambient atmosphere may induce a chemical reaction that results in an irreversible structural modification (for example, oxidation, reduction, or the alteration of surface stress of strain) and/or (2) The ambient atmosphere may be adsorbed on the metallic islands and form a surface dipole layer which can modify the charge carrier's tunneling barrier height, or be adsorbed in the gap regions and alter the trap density (for example, weakly-bound chemisorbed species).

The sorption-desorption reversibility characteristic associated with the changes in the electrical conductivity of the copper/cuprous oxide island films, for example, suggests that the second mechanism dominates the electronic transport process.

Figure 1:
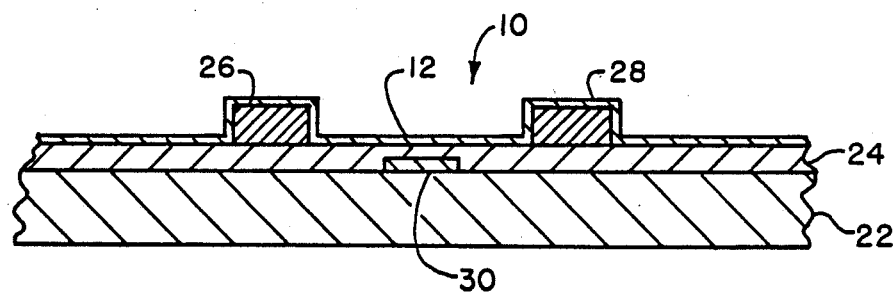
FIG. 1 illustrates, by cross-sectoion, the gas sensor of the present invention.
Figure 2A:
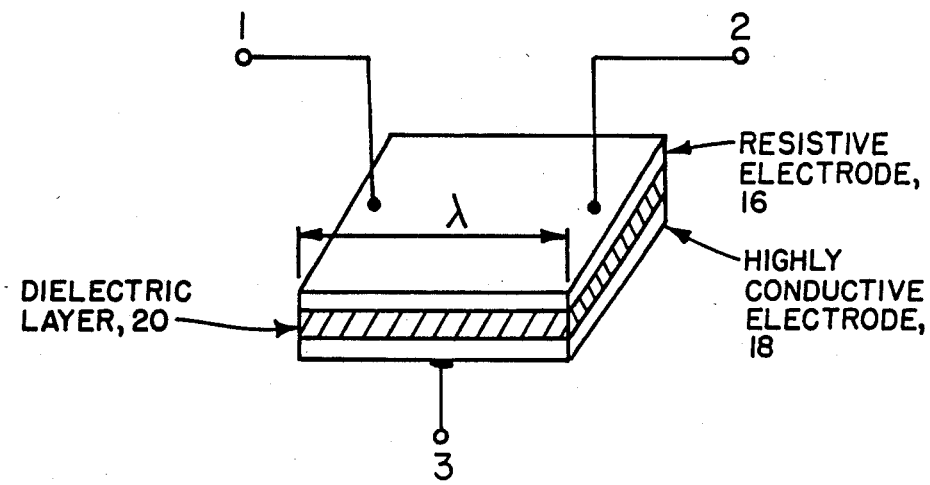
FIG. 2A illustrates schematically a device for implementing the RC notch network of the present invention.

Since the thermally evaporated, discontinuous copper/cuprous oxide films utilized have such high resistances (typically $10^6$–$10^8$ ohms), a sensor 10, FIG. 1, having a gas sensitive film 12 is a part of distributed RC notch network 14, FIG. 2, excited with a current source, and is compatible with large-valued, distributed resistances.

As shown in FIG. 1 a non-conductive substrate 22 has a metallic strip 30 thereon. A dielectric layer 24 is applied over strip 30 and substrate 22 and on top of layer 24 are applied two metallic strips 26 and 28 that are parallel to strip 30. The discontinuous metal gas sensitive film 12 is applied over the exposed dielectric layer 24 and strips 26 and 28. Electrical leads, not shown, are placed in appropriate positions.

Figure 2B:
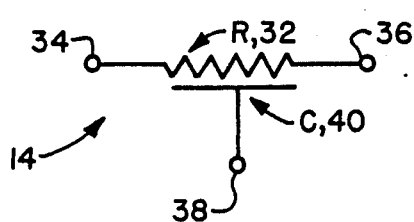
FIG. 2B illustrates an electrical schematic of the distributed RC notch networks.

To relate sensor 10 to distributed RC notch network 14, reference is made to FIG. 2, and, in particular, FIG. 2B. Distributed resistive element R 32 is provided by gas sensitive film 12 between strips 26 and 28. Strips 26 and 28 also act as contact points 34 and 36. Strip 30 acts as contact 38. The physical arrangement of strips 26, 28, and 30 and film 12 form the distributive capacitive element C 40 separate by dielectric layer 24.

Operation of the gas detector having sensor 10 therein is based on the following theoretical analysis. The distributed RC notch network 14 is a special case of the distributed RC low-pass electronic filter. That is, although the open-circuit voltage transfer function of the distributed RC low-pass filter is a meromorphic function, it is, nevertheless, possible to identify zeroes on the $j\omega$-axis. This result can be achieved with a judicious selection of lumped, passive elements that are appropriately configured with the fundamental distributed RC low-pass filter.

The types of immittances required to achieve this result are summarized in Table 1.

TABLE 1

| SUMMARY OF IMMITTANCES PRODUCING URC NOTCH NETWORK NULLS | | |
|---|---|---|
| $\delta$ (= RC) | $Z_s$ | $Y_p$ |
| $0 < \kappa < 11.19$ | R,L | −G,C |
| 11.19 | R | C |
| $11.19 < \kappa < 30.84$ | R,C | G,C |
| 30.84 | C | G |
| $30.84 < \kappa < 60.45$ | −R,C | G,L |
| 60.45 | −R | L |
| $60.45 < \kappa < 99.93$ | −R,L | −G,L |
| 99.93 | L | −G |

For $\delta > 99.93$, the entire pattern is repeated.

The foregoing analysis implies there is an infinite number of combinations of lumped, passive elements that will produce a notch or null on the $j\omega$-axis. To optimally realize sensor 10 application, the lumped resistor in series with the T-equivalent circuit was selected. That is, a specific lumped resistance value can be realized quite readily with a precision resistor, decade box, or a MOSFET operated as a voltage-variable resistor.

A schematic of the distributed RC notch network 14 configuration is depicted in FIG. 2. In the Laplace domain, the open-circuit voltage transfer function, written with conventional electrical notation, can be expressed as:

$$T(s) = \left.\frac{V_o(s)}{V_i(s)}\right|_{I_2(s)=0} = \frac{\alpha\xi + \sinh\xi}{\alpha\cosh\xi + \xi\sinh\xi} \quad (1)$$

where $\alpha = R/R_n$ is the notch parameter,
$\xi = (j\omega RC)^{1/2} = (j\delta)^{1/2} = (1+j)\gamma^{1/2}$,
$\gamma = (\omega/\omega_0)^{1/2}$,
$\delta = \omega RC$,
$\omega_0 = 2/RC$ The transfer function (gain) has a zero of transmission (notch or null) when the numerator of T(s) equals zero, that is:

$$\alpha + \xi \sin h\xi = 0. \quad (2)$$

The complex variable expression denoted in Equation (2) can be separated into two simpler relationships:

$$\tan \gamma = -(\tan h\gamma) \quad (3)$$

and $$\alpha = 2\gamma(\sin \gamma)(\cos h \gamma). \quad (4)$$

Since Equation (3) is a transcendental expression, it has an infinitely countable solution set denoted by $\{\gamma_n\}$. Only values of $\gamma$ corresponding to n-odd are significant since $\alpha$ is negative (physically impractical) for n-even. Because the gas sensitive film 12 resistance values are very large (on the order of $10^8$ ohms), practical realizations of $R_n$ suggest the consideration of higher-order solutions. The results for the first-six, odd-order solutions are summarized in Table 2.

TABLE 2

NORMALIZED CONSTANTS FOR ZEROES OF THE IDEAL URC NOTCH NETWORK

| Solution Iterate [n] | Normalized Notch Frequency $[2(\omega/\omega_o)]$ | Notch Resistance Ratio $[\alpha = R/R_n]$ |
| --- | --- | --- |
| 1 | $1.118664272560 \times 10^1$ | $1.779854240671 \times 10^1$ |
| 3 | $1.492777676373 \times 10^2$ | $3.451457715459 \times 10^4$ |
| 5 | $4.453658986441 \times 10^2$ | $3.192391643120 \times 10^7$ |
| 7 | $8.993676757813 \times 10^2$ | $2.429287416977 \times 10^{10}$ |
| 9 | $1.511283203125 \times 10^3$ | $1.686305061491 \times 10^{13}$ |
| 11 | $2.281112060547 \times 10^3$ | $1\ 109400336735 \times 10^{16}$ |

A small, but consistent error observed in the performance of the distributed RC notch network 14 configured as a gas sensor 10 is accounted for by considering the effect of dielectric loss. The influence of dielectric loss can be examined by introducing an incremental conductance $g_s(\omega)$ $[=r_s(\omega)^{-1}]$ in series with the incremental distributed capacitance (c).

The physically realistic roots (normalized notch frequency and notch resistance ratio parameters) are summarized in Table 3.

TABLE 3

TUNING PARAMETERS FOR A URC NOTCH NETWORK WITH DIELECTRIC LOSSES (Continued)

| Dielectric Loss Parameter $[\eta(\omega)=R_s(\omega)/R]$ | Solution Iterate [n] | Normalized Notch Frequency $[2(\omega/\omega_o]$ | Notch Resistance Ratio $[\alpha = R/R_n]$ |
| --- | --- | --- | --- |
| $1.5 \times 10^{-3}$ | 1 | $1.145884799957 \times 10^1$ | $1.891301208471 \times 10^1$ |
|  | 3 | $2.682390441895 \times 10^2$ | $3.749081753925 \times 10^6$ |
| $5 \times 10^{-3}$ | 1 | $1.221794319153 \times 10^1$ | $2.220782218770 \times 10^1$ |
| $1 \times 10^{-2}$ | 1 | $1.379062393188 \times 10^1$ | $2.996292709715 \times 10^1$ |
| $1.5 \times 10^{-2}$ | 1 | $1.680923652649 \times 10^1$ | $4.874677780074 \times 10^1$ |
| $1.845 \times 10^{-2}$ | 1 | $2.7071840059 \times 10^1$ | $1.617500213638 \times 10^2$ |

Figure 4:
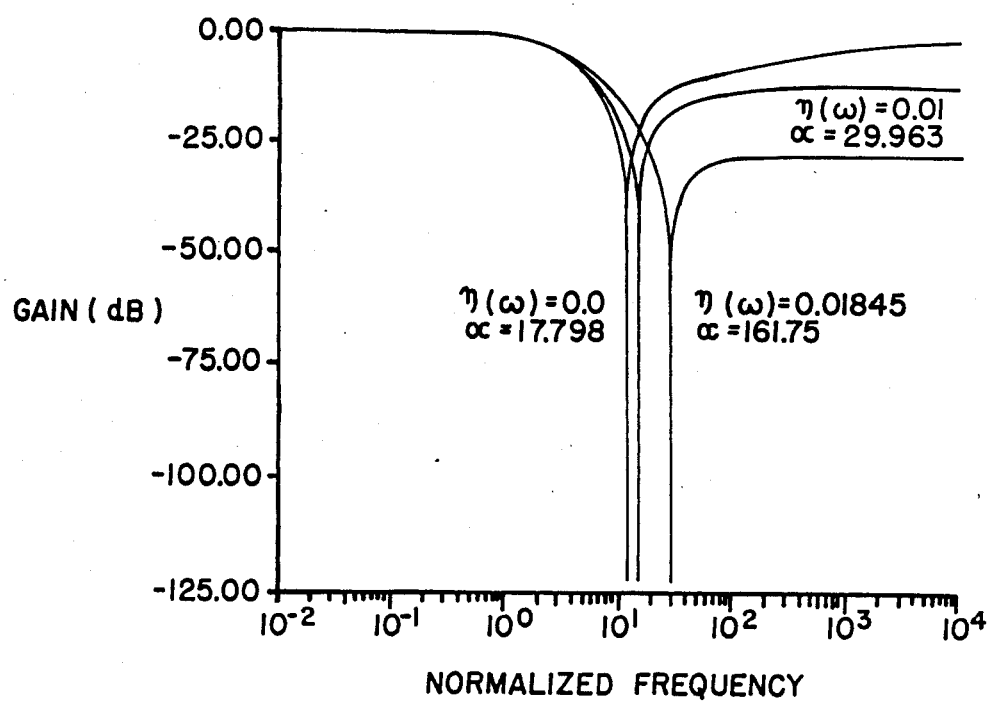
FIGS. 4 and 5 illustrate frequency versus gain of a distributed RC notch network.

FIG. 4 depicts the theoretical influence of dielectric loss on the first-order (n=1) solutions for the gain and phase response of the lossy distributed RC notch network 14 for several values of $\eta(\omega)$. The higher-order, n-odd plots are similar in form, but the normalized notch frequency is correspondingly translated along the horizontal axis.

With respect to the distributed RC notch network 14 in general, dielectric loss compensation is implemented utilizing the following procedure. To determine dielectric loss as a function of frequency, a parallel plate capacitor is fabricated adjacent to the distributed RC notch network sensor 10. This capacitor must have the same physical dimensions as the distributed capacitance of sensor 10. A frequency-variable, alternating current impedance bridge is then used to measure the dissipation factor (loss tangent) and capacitance ($C_s$) of the test capacitor as a function of frequency. Accordingly, $R_s(\omega)$ is determined from the following relationship:

$$\tan \delta = \omega R_s(\omega) C_s \qquad (5)$$

and plotted as a function of frequency. Next, the ideal theory of the distributed RC notch network 14, along with an independently measured value of its distributed resistance (R) and calculated value of its distributed capacitance (C), are used to estimate the critical notch parameters (notch frequency and notch resistance ($R_n$)). Then, in conjunction with the dielectric loss capacitor's $R_s(\omega)$ versus frequency plot, the sensor's theoretical notch frequency ($\omega_o=2/RCs$) utilized to interpolate an estimate of $R_s(\omega)$. Accordingly, the ratio of $R_s(\omega)$ to R specifies the dielectric loss parameter $[\eta(\omega)]$. Finally, interpolation between discrete values of $\eta(\omega)$ tabulated in Table 3, shown partially, is used to identify the dielectric loss compensated estimates of the notch frequency and notch resistance ($R_n$). This error correction facilitates identification of the critical tuning parameters for a synthesized sensor 10, particularly for the large corrections that are characteristic of a lossy dielectric and the need to operate the detector at one of the higher-order solutions.

The distributed RC notch network 14 can be readily configured as sensor 10 by utilizing the gas-sensitive, discontinuous copper/cuprous oxide film 12 as the network's distributed resistance electrode 16. Although the swept-frequency, alternating current excitation and processing electronics add a dimension of complexity to the operation compared to the more conventional direct-current differential operational amplifier circuit, the disadvantage of working with a large-valued distributed resistance that is an integral part of the RC notch network 14 is moot, since higher-order notch tuning parameter solutions can be selected that yield practical and attractive specifications for $R_n$. At the same time, the RC product can be independently tailored via the geometrical specification of C (cross-sectional area and dielectric thickness), and thus, a corresponding practical notch frequency can be simultaneously realized.

Once the tuning parameters have been specified, the distributed RC notch network 14 behavior as a sensor 10 is implemented via the following scenario:

(1) Initially, after dielectric loss corrections have been made, an unexposed sensor 10 is precisely tuned (vary $R_n$) to optimize the notch depth. The associated notch frequency and the value of $R_n$ comprise a set of reference values.

(2) Upon exposure to an organophosphorus compound, R changes (decreases). Accordingly, the RC product and the $\alpha$-ratio change. Therefore, a change in the magnitude of the notch depth (decrease) and notch frequency are observed. The change associated with the detuned notch frequency and notch depth parameters relative to the reference values can be readily calculated, and their magnitudes are found to correlate with the gas exposure concentration.

(3) In addition, once sensor 10 has shifted to a detuned state, the option for adjusting $R_n$ to re-establish the optimally tuned state is available. Accordingly, the magnitude of this change could also be used as a detection parameter. This detection mode is particularly advantageous when a voltage-variable MOSFET is utilized to realize $R_n$.

Figure 5:
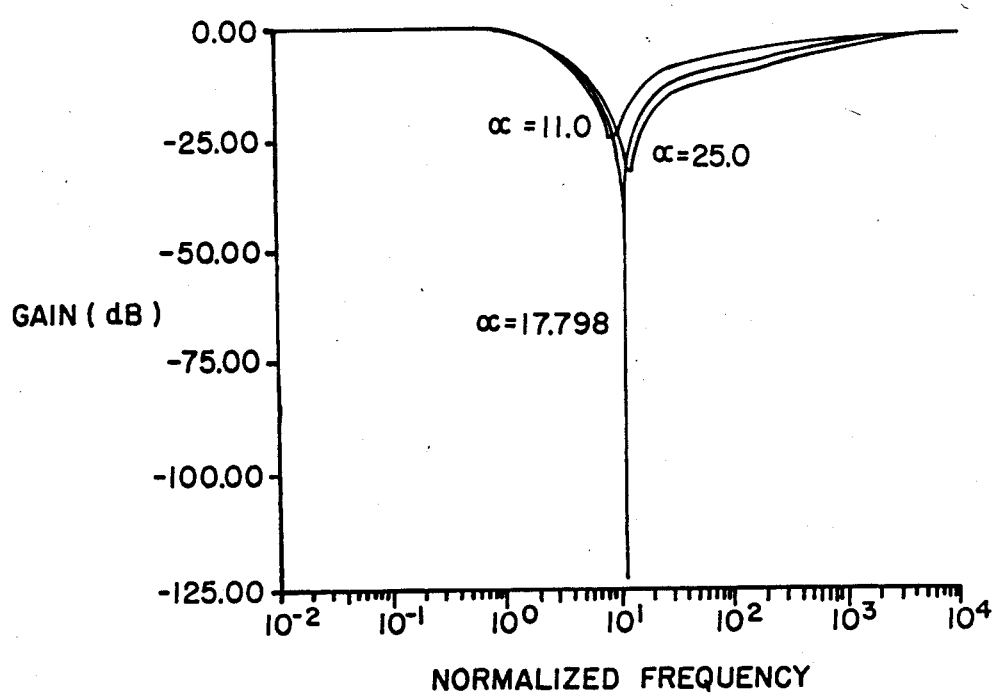

To illustrate these points, FIG. 5 depicts the theoretical influence of $\alpha$-variations with respect to the first-order (n=1) solution for the gain and phase response of the ideal distributed RC notch network 14. (The functional relationship between the curves is preserved when higher-order solutions and dielectric loss are considered).

In addition, this detection scheme has a distinct advantage when compared with competitive techniques, such as the mass-sensitive, coated piezoelectric crystal which detects adsorbed species by changing (decreasing) its resonant frequency. It is noted that either the species of interest or an interference could induce the same frequency change. However, the distributed RC notch network sensor 10 is more selective because it detects only adsorbed species that modify the electronic conductivity of the gas-sensitive film 12, and not just those that are adsorbed as an arbitrary mass change. Further, it is reasonable to expect that a certain number of potential interferences will increase the gas-sensitive film's resistance. Thus, the proposed operating scenario intrinsically discriminates against such responses according to the sign of the change associated with the notch frequency. Finally, it is recognized that all interferences may not be unambiguously rejected with a single sensor 10. Consequently, a clustered array of distributed RC notch network sensors 10, not shown, each with a different gas-sensitive film 12 and gas-response characteristic, could be readily configured on a single substrate and sequentially interrogated under the control of a microprocessor, not shown, to further enhance the specificity of this detector technology. Finally, compensation for temperature stability and other environmental effects can be accommodated by operating two identical distributed RC notch network sensors 10 in intimate proximity. One sensor 10 (active element) is isolated from the atmosphere under investigation, but is operated in a chamber whose atmosphere is similar, but void of the contaminant. Under these operating conditions, there will be at most a small, but constant performance differential between (notch frequency and notch depth) the two sensors 10 when both are operated in uncontaminated atmospheres, and this difference can be attributed to the fact that the two sensors 10 are not absolutely identical. This small differential will remain constant even with small environmental perturbations. However, the adsorption of the desired contaminant on the active sensor will act to drastically modify the magnitude of this differential and result in a positive alarm signal.

Two critical features of sensor 10 are the physical structure and composition of the thermally evaporated, gas-sensitive, copper/cuprous oxide films 12, and verification that diisopropyl methylphosphonate (DIMP) is adsorbed. Direct replica, transmission electron microscopy (TEM) and transmission electron diffraction (TED) were utilized to determine the gas-sensitive film's structure and composition. Auger electron spectroscopy (AES) was employed to independently verify that DIMP was adsorbed.

Figure 6:
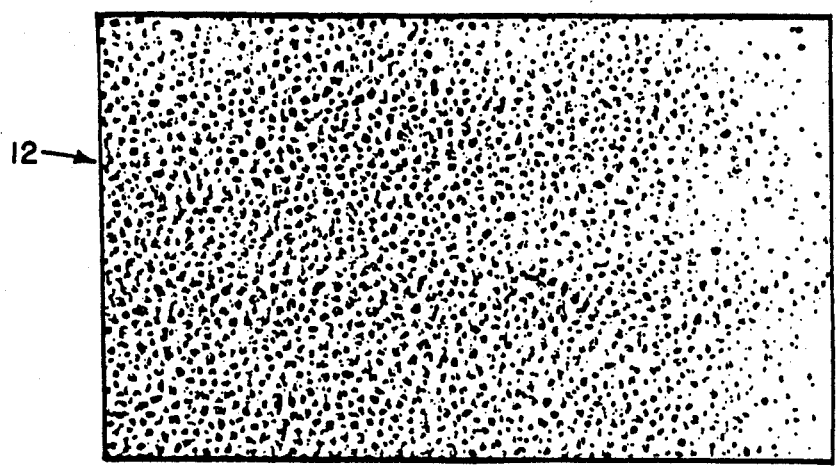
FIG. 6 illustrates the structure of the discontinuous film of the present invention.

A TEM micrograph of a 100 angstrom average thickness copper/cuprous oxide film is shown in FIG. 6. This Figure clearly illustrates the discontinuous and island-like nature of the gas-sensitive film 12. For the deposition technology, materials, and procedure utilized, the films remain discontinuous up to a thickness of approximately 200 angstroms.

TED analysis of the film was utilized to determine its qualitive chemical state and its physical structure. The analysis reveals a mixed phase of copper/cuprous oxide.

The motivation for the AES investigation of the dielectric supported copper/cuprous oxide island film structures exposed to parts-per-million (ppm) concentration levels of DIMP was to determine if and where the contaminant is adsorbed on the distributed resistance electrode structure. Specifically, the AES spectra for the electrode-gap, island-structure films supported on a silicon dioxide or silicon nitride dielectric layer 24 were obtained by probing several key locations on the surface. The criterion for concluding DIMP adsorption is the presence of a phosphorus (P) Auger transition since this element is not a common bulk or atmospheric contaminant, and is unique to the DIMP compound.

The pattern of behavior for both the silicon dioxide and silicon nitride dielectric layer 24 were indistinguishable. In addition, unexposed control specimens were independently analyzed, and no phosphorus Auger peak was discernable. Thus, for illustrative purposes, the preferred case has silicon nitride dielectric layer 24 for a supported film 12.

In order to ascertain whether the DIMP/water vapor complex is adsorbed on the exposed surface of the dielectric layer 24, an AES spectrum was initially obtained at a location outside the thermally evaporated, solid copper strip 30 (nominal 2000 angstrom thickness) and the gas-sensitive island film 12. As determined, the DIMP/water vapor complex is not strongly adsorbed on the silicon nitride dielectric layer 24 (similar results obtained for the silicon dioxide dielectric support).

To ascertain the adsorbance of the DIMP/water vapor complex on the islands themselves, a focused beam (less than 10 micron diameter) AES spectrum of the copper/cuprous oxide islands in the electrode gap region was performed. As anticipated, the silicon (Si) and nitrogen (N) peaks dominate the spectrum (silicon nitride dielectric support). But more importantly, the phosphorus (P) peak is still present. Therefore, the DIMP/water vapor complex is not adsorbed on the surface of the silicon nitride dielectric layer 24 (the silicon dioxide supported specimen reveals the same conclusion). Thus the copper/cuprous oxide islands are indeed active adsorption sites of DIMP.

In order to determine if the DIMP/water vapor complex is adsorbed solely on the surface or in the bulk of the gas-sensitive film 12, low-energy, inert ion sputtering was utilized. By additional analysis, therefore, it is concluded that the DIMP/water vapor complex is preferentially adsorbed on the surface of the copper/cuprous oxide islands.

In principle, a metallic surface may be treated in terms of a simple valency theory where the atoms or groups of atoms which comprise the surface differ fundamentally from those within the bulk. Specifically, the surface atoms cannot interact symmetrically with neighboring atoms and their effect causes an energy distribution imbalance. Consequently, surface atoms frequently exhibit unsaturated valences which are capable of forming a bond with foreign atoms or molecules. This process is known as adsorption. Further, adsorption is known to influence those phenomena which depend on the properties of surfaces. One of the most important properties is electrical conductivity.

For sensor 10, the measurements were devised to determine the characteristics of the gas-sensitive copper/cuprous oxide film 12 which maximizes changes in electronic conductivity with respect to DIMP exposure. This included resistance changes versus time, conductivity versus temperature, and current versus voltage. The relative percent change of resistance was calculated using:

$$\Delta = [(R - R_o)/R_o] \times 100 \tag{6}$$

where
- $\Delta$ is the relative percent change of resistance
- R is the resistance of the gas-sensitive film when exposed to a contaminant of interest
- $R_O$ is the pre-exposure resistant of the gas-sensitive film under the influence of a carrier gas flow, but void of the contaminant.

For a well regulated carrier component, a given DIMP challenge concentration not only affects the reaction rate (reaction rate increases with increasing DIMP concentration), but it also produces a substantial change in the gas-sensitive film's resistance. In addition, the response is reversible.

The criticality of the discontinuous film morphology is clearly emphasized when similar DIMP challenge results are compared with a thin, but continuous film 12. The response of an 800 angstrom average thickness copper/cuprous oxide film exposed to a 650 ppm DIMP concentration (2.1 percent relative humidity laboratory air carrier) challenge to equilibration is very long, and that $\Delta$ is approximately one-half that for the discontinuous film 12. In addition, continuous films reveal only marginal reversibility, and this effect disappears after approximately six successive challenge and purge cycles.

Therefore, it is concluded that the discontinuous film morphology, the metallic clusters, the dielectric layer 24 support, and the region between clusters is critically important for maximizing the gas adsorption behavior. In addition, the sigmoidal-shaped, gas adsorption response can be least-squares fitted to a conventional growth law that predicts how the fractional area between nucleating sites expands with adsorption. Since a change of resistance can be related to the change of the fractional area covered between nucleating sites with an empirical constant of proportionality (k), the conventional growth law can be recast as:

$$\Delta R/R_o = k[1 - \exp(-bt^3)] \tag{7}$$

where
- $\Delta R$ is the change of resistance caused by the adsorption of a contaminant,
- $R_o$ is the discontinuous film's resistance before exposure,
- k is an empirical constant of proportionality, and
- t is time.

It is well known that discontinuous metallic films have a negative temperature coefficient of resistance and that the film's resistance decreases exponentially with absolute temperature (thermally activated conduction process). Therefore, conductivity versus temperature measurements were made to determine if the adsorption of DIMP on the copper/cuprous oxide films is an activated process.

The results reveal several unusual, but consistent features in the semi-logarithmic current versus reciprocal absolute temperature plots obtained.

Analysis of the linear behavioral region (130° K. < T < 373° K.) reveals that the activation energy increases with decreasing film thickness, but that it remains essentially the same before and after exposure. Indeed, the superposition of unexposed and exposed plots reveal an incremental, but nearly uniform increase in the measured current throughout this temperature range. Therefore, it is postulated that the adsorption of the DIMP/water vapor complex manifests itself by redistributing or introducing additional trap and impurity sites with a comparable activation energy in the vicinity of the substrate's conduction band edge.

The low temperature (T < 130° K.), variable activation energy region reveals that DIMP exposure has virtually no effect.

The high temperature (T > 373° K.) variable activation energy behavior is characterized by a dramatic decrease in conductivity that occurs at approximately 100° C. and persists at temperatures as high as 200° C. Upon cooling to the ambient (22° C. and 42 percent relative humidity), the film's conductivity increases and equilibrates to within 3 percent of the value measured before the investigation was initiated. Therefore, it is postulated that this high-temperature departure from linearity is attributable to the thermal desorption of water vapor (note the critical 100° C. point), and the rejuvenation of the film's gas sensitivity is due to the re-adsorption of water vapor from the ambient. Thus, to maximize the sensor's performance, the discontinuous, gas-sensitive film 12 should be operated in the linear behavioral temperature region.

The final direct current measurements used to address the issue of maximizing gas sensitivity were isothermal current versus voltage experiments.

Quantitatively, the isotherms were least-squares fitted to a phenomenological relationship of the form:

$$I = A(T,g)V + B(T,g)V^2 \tag{8}$$

where
- I is the measured current,
- V is the applied direct current voltage,
- A(T,g) is the ohmic (linear) coefficient which may be a function of temperature (T) and DIMP exposure (g), and
- B(T,g) is the non-ohmic (non-linear) coefficient which may be a function of temperature and DIMP exposure.

Since it is desirable to operate the gas-sensitive structure under conditions (temperature, film thickness, and applied direct current bias) that maximize conductivity changes for the smallest increment of DIMP exposure, it is important to not only maximize the ($\Delta A/A$) and $\Delta B/B$) parameters, but also their relative ratio.

The results for the most sensitive film are summarized in Tables 4 and 5.

TABLE 4

LEAST-SQUARES CALCULATIONS OF THE COEFFICIENTS IN THE MODEL: $I = A(T,g)V + B(T,g)V^2$ FOR THE 72Å THIN FILM ELECTRODE STRUCTURES*

| Temperature (°C.) | Unexposed Film | | Exposed Film (10 mTorr Evacuation) | | Exposed Film (Atmospheric Pressure) | |
|---|---|---|---|---|---|---|
| | A(T,g) | B(T,g) | A(T,g) | B(T,g) | A(T,g) | B(T,g) |
| −20 | $4.142627 \times 10^{-9}$ | $4.183758 \times 10^{-11}$ | $4.382305 \times 10^{-9}$ | $4.3717959 \times 10^{-11}$ | $5.220928833 \times 10^{-9}$ | $4.6978139 \times 10^{11}$ |
| −10 | $5.071346 \times 10^{-9}$ | $4.199716 \times 10^{-11}$ | $5.248448 \times 10^{-9}$ | $4.394222 \times 10^{-11}$ | $6.015684983 \times 10^{-9}$ | $4.750482 \times 10^{-11}$ |
| 0 | $5.726941 \times 10^{-9}$ | $4.25562108 \times 10^{-11}$ | $6.00271915 \times 10^{-9}$ | $4.4574320 \times 10^{-11}$ | $7.182637217 \times 10^{-9}$ | $4.82592415 \times 10^{-11}$ |

TABLE 4-continued
LEAST-SQUARES CALCULATIONS OF THE COEFFICIENTS IN THE MODEL: $I = A(T,g)V + B(T,g)V^2$ FOR THE 72Å THIN FILM ELECTRODE STRUCTURES*

| Temperature (°C.) | Unexposed Film | | Exposed Film (10 mTorr Evacuation) | | Exposed Film (Atmospheric Pressure) | |
|---|---|---|---|---|---|---|
| | A(T,g) | B(T,g) | A(T,g) | B(T,g) | A(T,g) | B(T,g) |
| 10 | $6.793701 \times 10^{-9}$ | $4.310659 \times 10^{-11}$ | $7.134862 \times 10^{-9}$ | $4.6208027 \times 10^{-11}$ | $8.0245856 \times 10^{-9}$ | $4.909177567 \times 10^{-11}$ |
| 20 | $7.545314 \times 10^{-9}$ | $4.354977 \times 10^{-11}$ | $8.018109117 \times 10^{-9}$ | $4.8851086 \times 10^{-11}$ | $9.06089205 \times 10^{-9}$ | $5.402870417 \times 10^{-11}$ |
| 30 | $8.475004 \times 10^{-9}$ | $4.457771 \times 10^{-11}$ | $8.7666512 \times 10^{-9}$ | $5.10352663 \times 10^{-11}$ | $9.8425761 \times 10^{-9}$ | $5.743825667 \times 10^{-11}$ |
| 50 | $1.062419 \times 10^{-8}$ | $4.640461 \times 10^{-11}$ | $1.121581483 \times 10^{-8}$ | $5.673721067 \times 10^{-11}$ | $1.278221383 \times 10^{-8}$ | $6.671857233 \times 10^{-11}$ |
| 70 | $1.309584 \times 10^{-8}$ | $4.879482 \times 10^{-11}$ | $1.391194683 \times 10^{-8}$ | $6.23180 \times 10^{-11}$ | $1.540280783 \times 10^{-8}$ | $8.4036895 \times 10^{-11}$ |
| 90 | $1.532455 \times 10^{-8}$ | $5.085695 \times 10^{-11}$ | $1.63714865 \times 10^{-8}$ | $7.0698897 \times 10^{-11}$ | $1.791885733 \times 10^{-8}$ | $1.011668093 \times 10^{-10}$ |

*Averages for six structures reported.

TABLE 5
S-PARAMETER CALCULATIONS AND THE RELATIVE CHANGES IN THE COEFFICIENTS IN THE MODEL: $I = A(T,g)V + B(T,g)V^2$ FOR THE 72Å THIN FILM ELECTRODE STRUCTURES*

| Temperature (°C.) | Exposed Film (10 mTorr Evacuation) | | | Exposed Film (Atmospheric Pressure) | | |
|---|---|---|---|---|---|---|
| | $\left[\frac{\Delta A}{A}\right]$ | $\left[\frac{\Delta B}{B}\right]$ | S | $\left[\frac{\Delta A}{A}\right]$ | $\left[\frac{\Delta B}{B}\right]$ | S |
| −20 | $5.785652 \times 10^{-2}$ | $4.4945 \times 10^{-2}$ | 0.7768355 | $2.6029 \times 10^{-1}$ | $1.22875 \times 10^{-1}$ | 0.47205 |
| −10 | $3.4606 \times 10^{-2}$ | $4.6314 \times 10^{-2}$ | 1.33835 | $1.8621072 \times 10^{-1}$ | $1.3114363 \times 10^{-1}$ | 0.7042759 |
| 0 | $4.815471 \times 10^{-2}$ | $4.7422 \times 10^{-2}$ | 0.984784 | $2.541839 \times 10^{-1}$ | $1.3401171 \times 10^{-1}$ | 0.5272235 |
| 10 | $5.02173 \times 10^{-2}$ | $7.19481 \times 10^{-2}$ | 1.432735 | $1.8118027 \times 10^{-1}$ | $1.38846187 \times 10^{-1}$ | 0.76634276 |
| 20 | $6.26608 \times 10^{-2}$ | $1.2173 \times 10^{-1}$ | 1.94268 | $2.008635 \times 10^{-1}$ | $2.40619736 \times 10^{-1}$ | 1.1979266 |
| 30 | $3.44126 \times 10^{-2}$ | $1.44861 \times 10^{-1}$ | 4.209534 | $1.6136536 \times 10^{-1}$ | $2.884972483 \times 10^{-1}$ | 1.78785117 |
| 50 | $5.56866 \times 10^{-2}$ | $2.22663 \times 10^{-1}$ | 3.998502 | $2.0305499 \times 10^{-1}$ | $4.3775742 \times 10^{-1}$ | 2.1558565 |
| 70 | $6.23180 \times 10^{-2}$ | $2.63579 \times 10^{-1}$ | 4.229581 | $1.7616036 \times 10^{-1}$ | $7.2225033 \times 10^{-1}$ | 4.0999594 |
| 90 | $6.8318 \times 10^{-2}$ | $3.9015 \times 10^{-1}$ | 5.7108 | $1.6929 \times 10^{-1}$ | $9.8924 \times 10^{-1}$ | 5.8435 |

*Averages for six structures reported.

The behavorial trends associated with the ($\Delta A/A$), ($\Delta B/B$), and S parameters strongly suggest that the thinnest films (<80 angstroms), operated at slightly elevated temperatures (<100° C.) with an applied direct current bias greater than 10 volts, are the most gas sensitive. Finally, since the ($\Delta B/B$) parameter's performance is comparatively larger than the corresponding ($\Delta A/A$) parameter, it is concluded that the $B(T,g)$ coefficient's behavior dominates the electronic transport process.

In conclusion, the direct current experimental evidence suggests that carrier transport occurs via transitions between traps, impurities, and localized states in the dielectric layer 24 between the copper/cuprous oxide islands. This explanation is particularly advantageous because it is not necessary to raise an electron to the conduction band of the substrate, and since the tunneling distance between traps, impurity states, and localized states is small, tunneling between islands whose spacings are greater than 30 angstroms can be explained. Additionally, based upon the observed affinity of the metallic clusters for the DIMP/water vapor complex, it is reasonable to expect that the number and distribution of the trap and impurity states are influenced by the adsorption of this contaminant. Therefore, slow carrier transport between metallic islands is possible, and the experimental evidence suggests a thermally-activated process operating with a field emission mechanism. The linear $\ln A$ versus $T^{-1}$ plots support a strong thermally activated dependency and a weaker DIMP exposure sensitivity. On the other hand, the non-linear $\ln B$ versus $T^{-1}$ plots, strongly suggest that the $B(T,g)$ coefficient is both temperature and DIMP exposure sensitivite. This observation implies that the impurities and trap levels contributed by the adsorbed contaminant favorably enhance the shallow trap density in the substrate. Further, the experimental evidence suggests that these traps are readily accessible under high temperature and large field conditions. Finally, the reversibility feature of DIMP adsorption is attributed to the desorption of the trap states contributed by the DIMP/water vapor complex.

In addition to examining the effects of the discontinuous copper/cuprous oxide film's morphology, thickness, and critical operating parameters (temperature and direct current bias) that optimize gas sensitivity, the influence of an alternating current excitation and its affect on the design of the distributed RC notch network sensor is examined. These measurements are necessary because the direct current measurements characterize the charge transport between discrete metallic islands, and consequently, ignore the resistance of the individual metallic clusters. Fortunately, aternating current techniques afford the opportunity to analyze the conduction processes in both regions.

It is a well established experimental fact that the alternating current resistance of a discontinuous metallic film decreases as the frequency of excitation increases. This behavior is attributable to the presence of inter-island capacitance which is effectively shorted at high frequencies. A lumped-parameter equivalent circuit is used in the analysis. The circuit's three frequency independent components are a resistance, $R_c$, in series with a parallel combination of a resistance, $R_g$, and a capacitance, $C_g$. From a physical perspective, $R_c$ is associated with conduction in the metallic islands (intra-cluster), and $R_g$ and $C_g$ with conduction between clusters (in the gap region). At low frequencies, the measured resistance approaches the direct current resistance ($R_o = R_c + R_g$). At some frequency f ($=\omega/2\pi$), for which $(R_g)^{-1} << \omega C_g$, the metallic clusters are effectively shorted together and the measured resistance is that of the clusters ($R_c$) alone.

The thinnest film structures were found to be the most sensitive to DIMP exposure. In addition, the sensitivity analysis revealed that a large direct current bias (35 volts) and an operational temperature of 90° C. maximized gas sensitivity.

With respect to the distributed RC notch network design, it would be highly desirable to operate it over a frequency range where the change in resistance of the discontinuous copper/cuprous oxide film is maximized. The $R_p(f)$ versus frequency plot reveals two distinct regions:

1. $\lim_{f \to 0} R_p(f) = R_o = R_c + R_g$
2. $\lim_{f \to \infty} R_p(f) = R_c$ 2. The $\ln(R_g)$ and $\ln(R_c + R_g)$ versus reciprocal absolute temperature plots are linear with positive slopes which is indicative of discontinuous metallic film behavior. Also, the activation energies tend to increase with decreasing film thickness.

The effect of DIMP exposure on the two distributed RC notch network sensors was examined in terms of changes in the tuning parameters.

The thinnest film sensor (71 angstrom thickness) operated at 90° C. with a 35 volt direct current bias demonstrated the highest sensitivity toward DIMP.

In addition, a more comprehensive study was accomplished with the 71 angstrom thin film sensor operated at 90° C. with a 35 volt direct current bias relative to discrete concentration levels of DIMP spanning 1 to 650 ppm. The results are summarized in Table 6.

TABLE 6
PARAMETER CHANGES INVOKED BY DIMP EXPOSURE FOR THE DISTRIBUTED RC NOTCH NETWORK SENSOR (203 MICRON WIDE ELECTRODE GAP AND 71Å THIN FILM) OPERATED AT 90° C. WITH AN APPLIED DIRECT CURRENT BIAS OF 35 VOLTS

| DIMP Concentration (ppm) | [Notch Frequency $(f_n)(\times 10^3$ Hz)/ $\Delta f_\eta$(percent)*] | [Notch Resistance $(R_n)(\times 10^3$ ohms)/ $\Delta R_n$ (percent)*] | [Notch Depth (dB)/$\Delta$Notch Depth (percent)*] | [Electrode Resistance (R)($\times 10^7$ ohms)/ $\Delta$R (percent)**] |
|---|---|---|---|---|
| Unexposed* | [5.40/—] | [2.6591/—] | [87.2—] | [10.004/—] |
| 1 | [5.40/−0.027] | [2.5669/−3.153] | [84.2/−3.472] | [9.595/−3.186] |
| 10 | [5.39/−0.212] | [2.3799/−10.208] | [78.3/−10.236] | [8.987/−10.256] |
| 50 | [5.37/−0.582] | [2.3538/−11.193] | [77.5/−11.153] | [8.8880/−11.244] |
| 100 | [5.36/−0.767] | [2.3446/−11.540] | [77.1/−11.612] | [8.8510/−11.614] |
| 300 | [5.35/−0.952] | [2.3235/−12.336] | [76.4/−12.414] | [8.7690/−12.433] |
| 650 | [5.34/−1.137] | [2.3113/−12.796] | [76.4/−12.758] | [8.725/−12.872] |

*Exposed value
**Adjusted value to maximize notch depth upon exposure

Accordingly, the region where the phenomenological frequency effect association with the gap capacitance ($C_g$) can be avoided by not operating the distributed RC sensor in the frequency range where $R_p(f)$ makes a transition between the two limits discussed above. The experimental data for all three film thicknesses investigated suggest that the frequency range $4.5 \times 10^4$ Hz $\leq f \leq 6.0 \times 10^5$ Hz should be avoided.

It is observed that the $R_g$ parameter displays the greatest sensitivity toward DIMP exposure (approximately twice as much compared to the $R_c$ parameter at the optimum operating conditions). Therefore, it is most advantageous to operate the distributed RC notch network sensor in the lower frequency range ($0 \leq f \leq 4.5 \times 10^4$ Hz). In addition, this criteria will include the synergistic effect of DIMP exposure on the $R_c$ and $R_g$ parameters, while the influence of the gap capacitance ($C_g$) is minimized.

To complete the gas-sensitivity analysis of the 67 angstroms thick, discontinuous film 12, a comprehensive study of the film's response to discrete levels of DIMP spanning 0.1 ppm through 650 ppm was accomplished. Thus, the lower sensitivity limit appears to be on the order of 0.1 ppm of DIMP for a thin (<80 angstroms) discontinuous film operated at 90° C. with a large applied direct current bias level (at least 35 volts).

Finally, the behavior of the $R_c$, $R_g$, $C_g$, and ($R_c + R_g$) impedance parameters with respect to temperature were examined. For each of the three film thicknesses and both direct current bias levels, the following significant observations were noted:

1. The $\ln(R_c)$ versus reciprocal absolute temperature plots are linear with a negative slope which is indicative of metallic-like behavior.

Finally, the response-time behavior of the 71 angstrom thin film sensor operated under identical conditions was measured. The results in Table 7 summarize the response time of the sensor to a 650 ppm DIMP challenge.

TABLE 7
TIME RESPONSE RESULTS AND PARAMETER CHANGES INVOKED BY A 650 PPM DIMP EXPOSURE FOR THE DISTRIBUTED RC NOTCH NETWORK SENSOR (203 MICRON WIDE ELECTRODE GAP AND 71Å THIN FILM) OPERATED AT 90° C. WITH AN APPLIED DIRECT CURRENT BIAS OF 35 VOLTS

| Time Interval ($\Delta t$ = 30 sec) | Notch Frequency ($f_n$) ($\times 10^3$ Hz) | Notch Depth (dB) | $\Delta f_n$ (percent) | $\Delta$Notch Depth (percent) |
|---|---|---|---|---|
| 1* | 5.39 | 87.1 | — | — |
| 2 | 5.37 | 81.3 | −0.371 | −6.659 |
| 3 | 5.35 | 77.8 | −0.742 | −10.677 |
| 4 | 5.33 | 76.5 | −1.113 | −12.170 |
| 5** | 5.32 | 75.8 | −1.300 | −12.974 |

*Pre-exposure response (baseline) with $R_n$ = 2.648 × 10$^3$ ohms and R = 9.997 × 10$^7$ ohms.
**Equilibrated response with R = 8.706 × 10$^7$ ohms; retuning yielded $f_n$ = 5.38 × 10$^3$ Hz, $R_n$ = 2.3067 × 10$^3$ ohms, and a notch depth = 87.0 dB.

As the data reveals, a completely equilibrated response is attained in approximately 2 minutes.

Therefore, *it is concluded* that the direct and alternating current excitation studies support the position that the gas sensitivity of the dielectric supported discontinuous copper/cuprous oxide films is maximized for thin films (<80 angstroms), which a large direct current applied bias (at least 35 volts), operated at a temperature near 90° C., and excited at frequencies less than $4.5 \times 10^4$ Hz.

Sensor 10 was fabricated according to the procedure outlined in the next section. The critical operating frequency limit specified in the previous section (that is, $f < 4.5 \times 10^4$ Hz), and the trend toward maximizing gas-sensitivity for thin films, were regarded as constraints associated with the theoretical model of the device and are reflected in the resulting designs. The critical design parameters are summarized in Tables 8 and 9.

TABLE 8

EXPERIMENTAL RESULTS AND CALCULATED PARAMETERS FOR THE DISTRIBUTED RC NOTCH NETWORK SENSORS

| Parameter | Device Structure 1 | Device Structure 2 |
|---|---|---|
| Upper Electrode Gap Width ($\lambda$-parameter in Chapter IV) ($\mu$m) | 203 | 508 |
| Equivalent Distributed Gap Capacitance (C = c$\lambda$) (farads) | $49 \times 10^{-12}$ | $7.364 \times 10^{-10}$ |
| Measured Distributed Gap Resistance* (R = r$\lambda$) (ohms) | $1.160 \times 10^8$ | $8.506 \times 10^8$ |
| Calculated Characteristic Notch Frequency ($\omega_o = 2/RC$) (radians) | $3.5186 \times 10^2$ | 3.1929 |

*Experimental conditions: unexposed, 1.5 volt direct current bias, 20° C.

TABLE 9

IDEAL NOTCH NETWORK TUNING PARAMETER SOLUTION SET

| Iterate (n) | 203 $\mu$m Wide Electrode Gap Sensor | | 508 $\mu$m Wide Electrode Gap Sensor | |
|---|---|---|---|---|
| | $f_n$ (Hz) | $R_n$ (ohms) | $f_n$ (Hz) | $R_n$ (ohms) |
| 1 | $3.132317882 \times 10^2$ | $6.51738763 \times 10^6$ | 2.84237085 | $4.779043033 \times 10^7$ |
| 3 | $4.179854787 \times 10^3$ | $3.360898773 \times 10^3$ | $3.792941157 \times 10^1$ | $2.464465945 \times 10^4$ |
| 5 | $1.247047576 \times 10^4$ | 3.633639383 | $1.131613015 \times 10^2$ | $2.664460051 \times 10^1$ |
| 7 | $2.51827606 \times 10^4$ | $4.775062812 \times 10^{-3}$ | $2.2851686 \times 10^2$ | $3.5014383 \times 10^{-2}$ |

The metal stock used for the thermal evaporation of the discontinuous, gas-sensitive copper/cuprous oxide film 12 is available in the form of wire (0.5 mm in diameter) having a minimum purity of 99.999 percent. The insulating glass microscope slide substrates used to support the metallic films have a low sodium and metallic impurity content.

A conventional cleaning procedure removed organic and inorganic contamination from the glass microscope slides used as substrate 22.

Metal evaporation masks used to fabricate the dielectric loss test capacitor structures, were also used to define the shape of the gas-sensitive film's electrode strips 26, 28 and 30, and restrict the area covered by the deposition of the discontinuous copper/cuprous oxide film 12. The metal masks are fabricated from 0.889 mm thick aluminum stock that has been polished to a mirror lustre. A diamond-impregnated slitting saw is used to machine the long narrow channels. A simple mask with a 2.03 cm diameter hole is used to restrict the coverage of the thermally evaporated discontinuous films to the distributed resistance's electrode surfaces and their gap. Clearly, alternate techniques such as those used in semiconductor fabrication can be used to fabricate sensor 10 or a multiple of sensor 10.

A high-vacuum, thermal evaporation system (Veeco, model VE-7700, Plainview, NY 11803) is utilized to deposit the electrode strips 26, 28 and 30 and discontinuous, gas-sensitive films 12.

Figure 3:
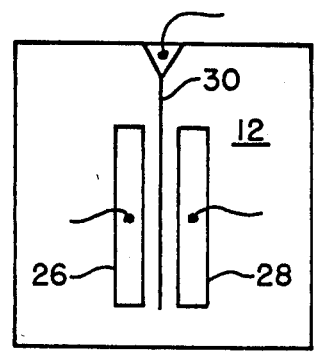
FIG. 3 illustrates, by a top view, the sensor of FIG. 1.

The planar electrode gap structures are fabricated using the following procedure:

A finished planar electrode structure is shown in FIG. 3 and is shown in the cross-section view of FIG. 1.

Aluminum lower electrode strip 30 is thermally evaporated (nominal 2000 angstrom thickness) onto the glass microscope slide substrate.

The Accuglass M3R and M3RP spin-on dielectric is applied to the surface of the evaporated lower electrode strip 30 and insulating substrate 22 with a pipette. A photoresist spinner is used to disperse the solution. The initial spread cycle is accomplished with a 500 rpm spin, lasting 3–4 seconds. The final dielectric film 24 thickness is achieved with a 20-second spin that spans 2000–5000 rpm (final spin speed depends upon the particular material and film thickness desired).

The appropriate upper electrode gap structure of strips 26 and 28 (solid copper) are thermally evaporated onto the surface of the dielectric film 29 (nominal 2000 angstrom thickness). Strips 26 and 28 are parallel and adjacent to strip 30.

After the solid copper electrode strips 26 and 28 are evaporated, the vacuum is broken and a direct current resistance measurement is made with an electrometer circuit. A clean gap has a resistance on the order of $10^{12}$ ohms and properly aligned strips have a coupling capacitance less than $10^{-16}$ farads.

The metal mask restricting the deposition of the discontinuous, gas-sensitive film 12 is positioned over the gap region between the solid copper electrode strips 26 and 28. After the copper/cuprous oxide island film 12 is deposited, the vacuum is broken and the resistance of the gap region is measured with an electrometer circuit. Satisfactory devices have resistances on the order of $10^8$ to $10^9$ ohms.

Lead wires are attached to the electrode strips 26, 28, and 30 using silver-filled conductive epoxy (Transene Company, Inc., type 50, Rowley, MA 01969). The mechanical robustness of the lead wire contacts is enhanced by securing a portion of the insulated lead wire to the inactive fringe area of the substrate with non-conductive epoxy.

Clearly, many modifications and variations of the present invention are possible in light of the above teachings and it is therefore understood, that within the inventive scope of the inventive concept, the invention may be practiced otherwise than specifically claimed.

What is claimed is:

1. A sensor for detecting a selected gas, said sensor operably connected to a detector for alerting a user to the presence of said selected gas, said sensor comprising:

a substrate, said substrate being electrically non-conductive and having a substantially flat upper surface;

a strip of metal, said strip being fixedly attached to said upper surface of said substrate, said strip having an electrical contact, said strip being rectangularly shaped, said strip of metal forming a first plate of a distributed capicitor of a distributed resistor-capacitor (RC) notch network;

a dielectric layer, said dielectric layer being fixedly attached over a selected area of said substrate and over said strip of metal, said dielectric layer being in the space between said first plate and a second plate of a capacitor of said distributed resistor-capacitor (RC) notch network;

a pair of strips of metal, said pair comprising a first strip of said pair and a second strip of said pair, said first and second strips of said pair being positioned on opposite sides of said strip attached to said substrate, said pair being fixedly attached to said dielectric layer and being equi-distant from and parallel to said strip attached to said substrate, said first and said second strip of said pair having an electrical contact thereon; and a gas sensitive film fixedly attached over said pair of strips and said dielectric layer, said gas sensitive film changing electrical conductivity when reacting with said selected gas wherein said gas sensitive film is a discontinuous copper/cuprous oxide film, said discontinuous copper/cuprous oxide film being a resistive material to form a distributed resistance of said distributed resistor-capacitor (RC) notch network and further being said second plate of said capacitor;

whereby said substrate, said strip attached to said substrate, said pair of strips, said dielectric layer, and said gas sensitive film form said distributed resistor-capacitor (RC) notch network within said detector so that when said selected gas reacts with said gas sensitive film the operating frequency at said notch shifts to a different operating frequency, a difference between said frequencies being related to the detection of said selected gas at a given level of concentration of said selected gas.

2. A sensor as defined in claim 1 wherein said discontinuous copper/cuprous oxide film has a thickness of less than 80 angstroms.

3. A sensor as defined in claim 1 wherein said selected gas contains therein organophosphorus compounds.

4. A sensor as defined in claim 1 wherein said substrate is non-conducting glass, said strip upon said substrate is copper with a thickness of about 2000 angstroms, and said first and said second strips are aluminum having a thickness of about 2000 angstroms.

* * * * *